United States Patent
Davis, III

(10) Patent No.: US 10,006,873 B1
(45) Date of Patent: Jun. 26, 2018

(54) DUAL-ENERGY MICROFOCUS RADIOGRAPHIC IMAGING METHOD FOR MEAT INSPECTION

(71) Applicant: BATELLE MEMORIAL INSTITUTE, Columbus, OH (US)

(72) Inventor: Richard J. Davis, III, Hilliard, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 0 days. days.

(21) Appl. No.: 15/379,071

(22) Filed: Dec. 14, 2016

(51) Int. Cl.
*G01N 23/06* (2006.01)
*G01N 23/04* (2018.01)
*G01N 33/12* (2006.01)
*G08B 21/18* (2006.01)

(52) U.S. Cl.
CPC ............. *G01N 23/04* (2013.01); *G01N 33/12* (2013.01); *G08B 21/18* (2013.01); *G01N 2223/206* (2013.01); *G01N 2223/401* (2013.01); *G01N 2223/408* (2013.01); *G01N 2223/618* (2013.01); *G01N 2223/652* (2013.01)

(58) Field of Classification Search
CPC ............. G08B 21/18; G01N 2223/401; G01N 2223/618; G01N 2223/652; G01N 2223/206; G01N 23/20083; G01N 33/12; G01N 23/04; G01N 2223/408
See application file for complete search history.

(56) References Cited

U.S. PATENT DOCUMENTS

| 5,428,657 | A | * | 6/1995 | Papanicolopoulos ........... G01N 23/20083 378/86 |
| 5,841,833 | A | | 11/1998 | Mazess et al. |
| 6,285,740 | B1 | | 9/2001 | Seely et al. |
| 6,370,223 | B1 | * | 4/2002 | Gleason ................. G01B 15/00 378/54 |
| 6,449,334 | B1 | * | 9/2002 | Mazess .................. G01N 23/06 378/53 |
| 6,597,759 | B2 | * | 7/2003 | Mazess .................. G01N 23/06 378/53 |

(Continued)

FOREIGN PATENT DOCUMENTS

| EP | 1447454 | 8/2004 |
| EP | 1651111 | 7/2009 |

(Continued)

OTHER PUBLICATIONS

De Chiffre et al.; "Industrial applications of computed tomography"; CIRP Annals, vol. 63, No. 2, 2014.

(Continued)

*Primary Examiner* — Courtney Thomas
(74) *Attorney, Agent, or Firm* — Richard M. Klein; Fay Sharpe LLP

(57) ABSTRACT

A system and method for foreign object detection in meat processing is provided. The system and method combine microfocus X-ray tubes with dual energy X-rays to detect foreign objects in meat products. A dual energy image processing algorithm analyzes the dual energy X-rays passed through the meat product to identify the foreign object present therein. An alarm or other notification is then generated in response to the detection of a foreign object.

25 Claims, 9 Drawing Sheets
(6 of 9 Drawing Sheet(s) Filed in Color)

(56) References Cited

U.S. PATENT DOCUMENTS

| | | | |
|---|---|---|---|
| 6,600,805 B2 | 7/2003 | Hansen | |
| 6,636,827 B2 | 10/2003 | Sakagami | |
| 6,786,096 B2 | 9/2004 | Bond et al. | |
| 6,973,161 B2 | 12/2005 | Ohtsuki | |
| 7,060,981 B2 | 6/2006 | Retterath et al. | |
| 7,561,663 B2 | 7/2009 | Watanabe et al. | |
| 8,284,895 B1 | 10/2012 | Haff | |
| 8,351,672 B2 | 1/2013 | Tao | |
| 8,964,939 B2 | 2/2015 | Suvama et al. | |
| 9,095,146 B2 | 8/2015 | Sigurdsson et al. | |
| 9,307,774 B2 | 4/2016 | Sigurdsson et al. | |
| 9,364,191 B2 | 6/2016 | Ning et al. | |
| 2004/0120456 A1* | 6/2004 | Ellenbogen | G01V 5/0025 378/57 |
| 2005/0226376 A1* | 10/2005 | Yun | G01T 1/2018 378/62 |
| 2005/0287252 A1* | 12/2005 | Schrock | G01N 23/06 426/231 |

FOREIGN PATENT DOCUMENTS

| | | |
|---|---|---|
| WO | WO 01/96844 | 12/2001 |
| WO | WO 2005013826 | 8/2003 |
| WO | WO 2006004635 | 1/2006 |

OTHER PUBLICATIONS

Hildur Einarsdottir et al.; "Image Analysis for X-ray Imaging of Food"; XP055449481; May 31, 2016.

Nachiket Kotwaliwale et al.; "X-ray imaging methods for internal quality evaluation of agricultural produce"; Journal of Food and Science Technology; vol. 51, No. 1; Aug. 13, 2011.

J.P. Brienne et al.; "Assessment of meat fat content using dual energy X-ray absorption"; Meat Science; vol. 57, No. 3, Mar. 1, 2001.

Margareth Kazuyo Kobayashi Dias Franco et al.; "Microfocus X-ray imaging of Brazil nuts for quality control"; Semina: Ciencias Agrarias; vol. 36 No. 4; Aug. 1, 2015.

Josh Cowling et al; "Detecting bone fragments in meat products"; XP055450446; Jan. 1, 2016.

International Search Report dated Feb. 22, 2018 for corresponding application No. PCT/US2017/066429.

International Search Report dated Feb. 23, 2018 for corresponding application No. PCT/US2017/066445.

* cited by examiner

DUAL-ENERGY MICROFOCUS RADIOGRAPHIC IMAGING METHOD FOR MEAT INSPECTION

BACKGROUND

The following relates generally to the food processing arts, the meat processing arts, the radiographic imaging arts, the food safety arts, and the like. It finds particular application in conjunction within the meat and poultry processing industries, and will be described with particular reference thereto. However, it will be understood that it also finds application in other usage scenarios and is not necessarily limited to the aforementioned application.

In the food processing industry, particularly in the processing of meats and poultry, quality control involves the detection of any contaminants. Of particular concern is the presence of bones or other hard tissues, as well as foreign bodies such as glass, plastic, wood and metal, that impact the quality of a food product, as well as cause consumption safety concerns.

With respect to poultry and meats, processing of the respective animals, particularly the sawing and boning processing, can result in the presence of bone fragments. These fragments may not only decrease the value of the meat or poultry product, but also create a risk of harm through the consumption of the product by the consumer.

Various techniques currently available for detecting the presence of bone or other contaminants in meat products require laboratory testing of samples, which while suitable for detecting fat content, fail to analyze the entire product. Attempts to utilize radiographic techniques have met with limited success. The problems arise because while the entire product can be analyzed, attenuation of X-rays emitted in radiographic techniques require all other variables involved to be carefully controlled, e.g. product thickness, product fat content, density, etc. Furthermore, the detection of bone fragments, particularly those of poultry, is difficult to make due to the small size of such fragments and the density of poultry bones as opposed to non-avian species. In particular, use of radiographic techniques in young bird processing presents a unique challenge, as the bones in such young birds have not calcified to a point where the density of the bone is substantially different than the surrounding meat. For example, in the processing of poultry products, companies such as Baiada Poultry Pty. Ltd., of New South Wales, Australia, have long recognized this issue. Baiada Poultry Pty. Ltd. And Dr. Anthony Pavic have been leaders in seeking a solution to the detection of bones or other hard tissues and foreign bodies in poultry, including support and funding of development which has led, in part, to the present application.

There is therefore a need for a system and method that increases the probability of detecting unwanted debris in products.

BRIEF DESCRIPTION

According to one embodiment, there is provided a system for foreign object detection in poultry processing. The system includes a first microfocus X-ray tube outputting a first X-ray energy, and a second microfocus X-ray tube outputting a second X-ray energy, the second X-ray energy differing from the first X-ray energy. The system also includes at least one radiation detector positioned opposite the first and second microfocus X-ray tubes to receive dual energy X-rays emitted by the first and second microfocus X-ray tubes through an associated poultry product. In addition, the system includes an image processing system including a processor in communication with memory. The memory stores instructions which are executed by the processor causing the processor to receive an output from the at least one radiation detector of the dual energy X-rays through the associated poultry product, determine, in accordance with a dual energy algorithm, a presence of a foreign object in the associated poultry product, and generate an alarm responsive to determining the presence of the foreign object in the associated poultry product.

In accordance with another embodiment, there is provided a method for foreign object detection in poultry processing. The method includes emitting, through a first microfocus X-ray tube, X-rays at a first energy level through an associated poultry product, and emitting, through a second microfocus X-ray tube, X-rays at a second energy level through the associated poultry product with the first energy X-rays and the second energy X-rays combined as dual energy X-rays and with the first energy level different from the second energy level. The method further includes receiving, via at least one radiation detector, the dual energy X-rays transmitted through the associated poultry product and analyzing, with a processor in communication with memory storing a dual energy image processing algorithm, the dual energy X-rays received by the at least one radiation detector to identify a foreign object contained therein. Furthermore, the method includes generating, in response to the analysis, an alarm indicative of a presence of a foreign object in the associated poultry product.

In another embodiment, there is provided a system for foreign object detection in meat processing that includes at least one microfocus X-ray tube, at least one radiation detector, and an image processing system. The radiation detector is positioned opposite the at least one microfocus X-ray tube to receive dual energy X-rays emitted by the at least one microfocus X-ray tube through an associated meat product. The image processing system includes a processor in communication with memory, the memory storing instructions which are executed by the processor causing the processor to receive an output from the at least one radiation detector of the dual energy X-rays through the associated meat product, determine, in accordance with a dual energy algorithm, a presence of a foreign object in the associated meat product, and generate an alarm responsive to determining the presence of the foreign object in the associated meat product.

In accordance with another embodiment, there is provided a method for foreign object detection in meat processing that includes emitting, via at least one microfocus X-ray tube, dual energy X-rays through an associated meat product, and receiving, via at least one radiation detector, the dual energy X-rays transmitted through the associated meat product. The method further includes analyzing, with a processor in communication with memory storing a dual energy image processing algorithm, the dual energy X-rays received by the at least one radiation detector to identify a foreign object contained therein. In addition, the method includes generating, in response to the analysis, an alarm indicative of a presence of a foreign object in the associated meat product.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The subject disclosure may take form in various components and arrangements of component, and in various steps and arrangement of steps. The drawings are only for purposes of illustrating the preferred embodiments and are not to be construed as limiting the subject disclosure.

DETAILED DESCRIPTION

Figure 1:
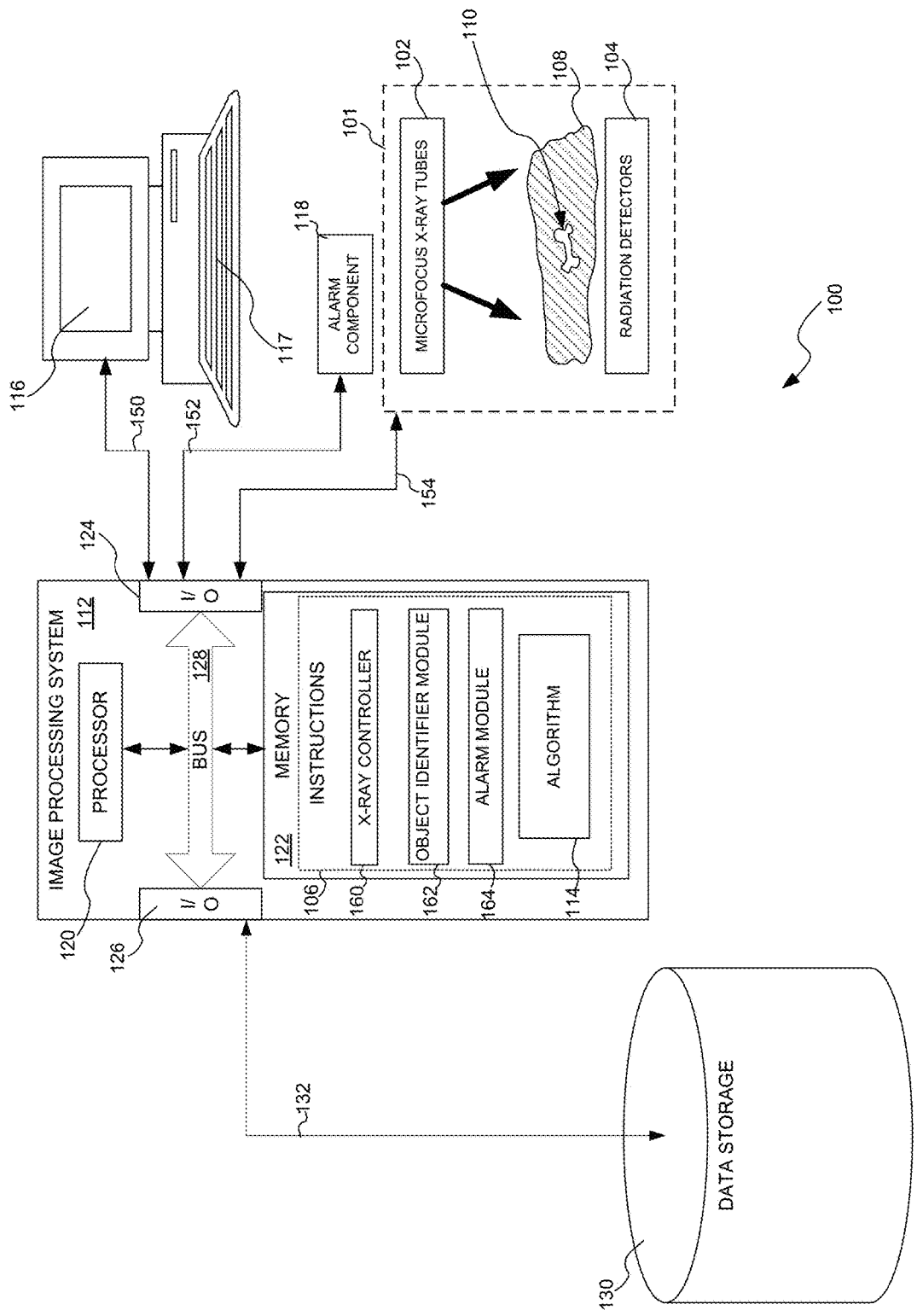
FIG. 1 is an illustration of a system for detecting foreign objects in meat and poultry products in accordance with one embodiment of the subject application.

One or more embodiments will now be described with reference to the attached drawings, wherein like reference numerals are used to refer to like elements throughout. Aspects of exemplary embodiments related to systems and methods for meat and poultry processing are described herein. In addition, example embodiments are presented hereinafter referring to young poultry bone detection and the like, however, application of the systems and methods set forth can be made in other areas, as will be appreciated by those skilled in the art. It will be appreciated that microfocus capabilities have not previously been utilized in the meat and poultry processing industry. Furthermore, although multi-energy images have been incorporated into some inspection equipment, a dual-energy approach, which makes use of the differences between the images-factoring the physical differences in energetic interactions, has not. Accordingly, the systems and methods disclosed herein employing the combination of microfocus techniques and dual-energy approach will increase probability of detection, especially for smaller-sized foreign objects.

In accordance with one embodiment of the subject disclosure, there is provided a system and method combining dual-energy X-ray beams with microfocused X-ray tubes for detecting debris in a meat or poultry product. The microfocused X-ray tube may utilize a micrometer-size focal spot which is combined by the systems, methods and algorithms described hereinafter with dual-energy imaging and detection to detect small foreign objects, e.g., less than 1 cubic millimeter piece of bone or cartilage in a meat or poultry product having a low response time, e.g., less than one second detection during meat inspections.

Turning now to FIG. 1, there is shown a system 100 for detecting contaminants in a meat product utilizing microfocus X-ray tubes, dual-energy X-ray beams, and dual-energy image processing algorithms in accordance with one embodiment of the subject disclosure. It will be appreciated that the various components depicted in FIG. 1 is for purposes of illustrating aspects of the exemplary hardware, software, or a combination thereof, are capable of being substituted therein. As depicted in FIG. 1, the system 100 includes at least one inspection system 101 in communication via a suitable communications link 154 with an image processing system 112, as described below. A suitable communications link 154 may include, for example, any suitable channel of data communications such as wireless communications, for example Bluetooth, WiMax, 802.11a, 802.11b, 802.11g, 802.11(x), a proprietary communications network, infrared, optical, the public switched telephone network, or any suitable wireless data transmission system, or wired communications.

As shown in FIG. 1, the inspection system 101 comprises one or more microfocus X-ray tubes 102 positioned opposite a radiation detector 104 and configured to emit X-rays 106 through a product 108 to detect a foreign object 110. As will be appreciated by those skilled in the art, a microfocus X-ray tube 102 as included herein may generate very small focal spot sizes, typically below 50 μm in diameter. The microfocus X-ray tube 102 utilized in the subject system 100 may comprise, for example and without limitation, a solid-anode tube, a metal-jet-anode tube, or the like. Examples of suitable microfocus X-ray tubes 102 capable of being used in the system 100 include, for example and without limitation: the high-resolution Y.FXE microfocus X-ray tubes from YXLON, models FXE-160 and FXE-225; the X-RAY WorX high-resolution microfocus transmission X-ray tubes, models in the T, TC, THE, and TCMF series; Hamamatsu Photonics' microfocus X-ray tubes, the L-series; and the Excillum MetalJet D2 series of micro-focus X-ray tubes.

As will be appreciated, the microfocus X-ray tube 102 of the subject disclosure enables smaller objects, i.e., foreign object 110, to be detected with a higher probability of detection as defined by the ability to detect the smaller object with higher radiographic contrast. As will be appreciated, while standard X-ray tubes have a focal spot size of 1.5 mm, which limits detection to objects of that size or greater, the microfocus X-ray tube 102 utilized in the subject systems and methods provide focal spot size of 15 to 50 micrometers. Accordingly, the microfocus X-ray tube 102 of the subject disclosure allows for substantial image magnification relative to conventional X-ray tubes, allowing smaller items to be detected with better contrast with respect to surrounding tissue.

The radiation detector 104 may be a small-pixel X-ray detector whose pixel size is comparable to the microfocus X-ray tube's spot-size 102 so as to enable small object detection with high probability of detecting such an object. [Radiation detectors can be of a either a line-scan or flat-panel type capable of detecting the energy ranges necessary for the dual-energy process, simultaneously or sequentially sourced with pixel resolution on the order of the micro-focus X-Ray tube size. Examples of suitable radiation detectors 104 capable of being used in the system 100 include, for example and without limitation: the Hamamatsu Photonics Dual energy X-ray line scan camera, series C10800-; the X-Scan Imaging Corporation's XID8800 Series Line-Scan Camera, and the Varian's amorphous silicon sensor panels, PaxScan's series. In accordance with one implementation of the subject system 100, the radiation detector 104 is positioned opposite the microfocus X-ray tube 102, whereupon the product 108 transits therebetween. Conveyance means for the product 108, as will be appreciated by those skilled in the art may include, for example and without limitation, a conveyor belt, chute, ramp, slide, rotary table, rollers, or myriad other conveyance means known in the art to transport the product 108 between the tube 102 and detector 104 for detection of foreign objects 110.

It will be appreciated that the dual energy X-ray beams 106 emitted by the microfocus X-ray tube 102 combine two radiographs at two distinct energies. According to one embodiment, the dual energy X-ray beams 106 combine two radiographs acquired at two distinct energies, calibrated for the meat and foreign-object desired. Accordingly, each radiograph separately provides an analysis of the product 108 with various contrasts between the meat or poultry product 108 and any foreign contaminates/objects 110 of interest. Combined, utilizing the dual-energy algorithms 114 of the subject application, the resultant imaging provides the capability of selectively imaging relevant materials of interest, namely meat product 108 and foreign objects 110, i.e., contaminates. For example, energy dependent differences of a bone versus meat are determined by energy spectra differences used for acquiring independent images. This reveals both the material density and the atomic number of both the meat/poultry product 108 and the foreign-object 110. Examples of foreign objects 110 that may contaminate the meat product 108 may include, for example and without limitation, bone fragments, cartilage, metal fragments, or the like. It will be understood that when properly calibrated for energy and material type, the dual energy X-rays 106 provide the material composition information and improved image contrast during foreign object detection.

The image processing system 112 may be implemented as illustrated in FIG. 1. It will be appreciated that the system 112 of FIG. 1 is capable of implementation using a distributed computing environment, such as a computer network, which is representative of any distributed communications system capable of enabling the exchange of data between two or more electronic devices. It will be further appreciated that such a computer network includes, for example and without limitation, a virtual local area network, a wide area network, a personal area network, a local area network, the Internet, an intranet, or the any suitable combination thereof. Accordingly, such a computer network comprises physical layers and transport layers, as illustrated by various conventional data transport mechanisms, such as, for example and without limitation, Token-Ring, Ethernet, or other wireless or wire-based data communication mechanisms. Furthermore, while depicted in FIG. 1 as a networked set of components, the system and method are capable of implementation on a stand-alone device adapted to perform the methods described herein.

As shown in FIG. 1, the image processing system 112 is capable of implementing the exemplary method described below. The image processing system 112 may include a computer server, workstation, personal computer, programmable logic controller, glide-station, laptop computer, cellular telephone, tablet computer, industrial controller, combination thereof, or other computing device capable of executing instructions for performing the exemplary method.

According to one example embodiment, the image processing system 112 includes hardware, software, and/or any suitable combination thereof, configured to interact with an associated user, a networked device, networked storage, remote devices, or the like. The exemplary image processing system 112 includes a processor 120, which performs the exemplary method by execution of processing instructions 124 which are stored in memory 122 connected to the processor 120, as well as controlling the overall operation of the image processing system 112.

The instructions 124 include an X-ray controller 160 configured to control the emission of X-rays by the microfocus X-ray tubes 102 in accordance with one embodiment of the subject application. In one embodiment, the X-ray controller 160 controls the microfocus X-ray tubes 102 to emit an X-ray at a first energy level and an X-ray at a second energy level (i.e., the dual energy X-rays 106) through a product 108 so as to enable detection of the foreign object 110 via the radiation detectors 104. The high and low energies (X-rays 106) from the dual-energy X-ray source, i.e., the microfocus X-ray tubes 102, are determined via the desire to produce the greatest contrast between the product 108 and the foreign object of interest 110 (e.g., bone, cartilage, glass, wood and plastic). In accordance with varying implementations of the subject systems and methods, the two energy ranges may comprise, for example and without limitation, a low energy range of 60-80 keV and a high energy range between 90-110 keV. Example implementations and simulations of the subject systems and methods illustrate the aforementioned exemplary ranges, as discussed in greater detail below.

The instructions 124 further include an object identifier module 162 configured to receive output from the radiation detectors 104 and to identify the foreign object 110 contained in the product 108 being scanned. In accordance with one embodiment, the object identifier module 162 utilizes data stored in the data storage 132 in conjunction with the algorithm 114 to determine whether a foreign object 110 is present in the product 108, as discussed in greater detail below. According to one embodiment, the object identifier module 162 is further configured to identify the type of foreign object 110 present in the product 108, e.g., bone, cartilage, metal, plastic, glass, wood, etc. It will be understood that each of these foreign objects 110 has radiographic set of parameters different than the product 108 (e.g., meat or poultry). These differences can be maximized by proper selection of energy output by the microfocus X-ray tubes 102. Furthermore, these radiographic differences may be enhanced with use of the dual-energy methodology set forth herein. Accordingly, proper employment of the micro-focus X-Ray tubes 102 enables application of this method to smaller foreign objects 110.

The instructions 124 of the image processing system 112 may further include an alarm module 164 configured to receive an output from the object identifier module 162 indicating a type of foreign object 110 detected in the product 108 and, based upon the type of foreign object 110, to activate an alarm component 118 coupled to the image processing system 112 via a suitable communications link 152. A suitable communications link 152 may include, for example, any suitable channel of data communications such as wireless communications, for example Bluetooth, WiMax, 802.11a, 802.11b, 802.11g, 802.11(x), a proprietary communications network, infrared, optical, the public switched telephone network, or any suitable wireless data transmission system, or wired communications.

In varying embodiments of the subject application, the alarm component 118 may be implemented as a speaker, display, a visual indicator (LED light, flashing light, etc.), text alert, audible alert, automated extractor/expeller to remove/expel the object 110, or other sensory device to alert an operator as to the presence and/or type of foreign object 110 present in the product 108. For example, in the event the object identifier 162 identifies the foreign object as metallic, one type of alert may be made via the alarm component 118, whereas if the foreign object 110 is identified by the module 162 as bone fragment, a different type of alert is made via the alarm component 118. Such alarms from detecting a foreign object 110, may consist in part or in whole, as an automated mechanical system to remove the contaminated product 108 and a notification made to a monitoring user, with various audible and visible alarms systems as may be desired by the end user.

As indicated above, the memory 122 further stores at least one dual-energy image processing algorithm 114 to executed by the processor 120 of the image processing system 112 to identify the foreign object 110 of interest. In accordance with one embodiment, the algorithm 114 is based on the dual-energy subtraction methodology which takes advantage of differences in the degree to which the meat 108 and contaminate 110 attenuate low- and high-energy (measured in tube voltage) X-rays 106. These differences are used to generate selective dual energy images. In an effort to increase probability of detection for smaller contaminates, the algorithm 114 factors in the microfocus aspects of the X-ray generator (e.g., spot-size), i.e., the microfocus X-ray tubes 102, detector 104 characteristics (e.g., pixel size) and radiographic geometry of the system 100.

With the above, the algorithm 114 can be applied to any type of dual-energy systems, including, but not limited to, a single-exposure system and a dual-exposure system. It will be understood that in single-exposure systems, one radiograph is obtained by exposing two radiation detectors 104 separated by a radiographic filter (not shown). The front detector receives the whole, unfractionated energy beam, which produces the low energy image. The radiographic filter select out lower-energy photons such that the back detector receives mostly higher-energy photons. In dual-exposure systems, two sequential radiographs are obtained at a low- and a high-energy, respectively. The high energy exposure is used to produce the high energy image, and vice versa. There is a small (~200-millisecond delay) between the two exposures.

Figure 2:
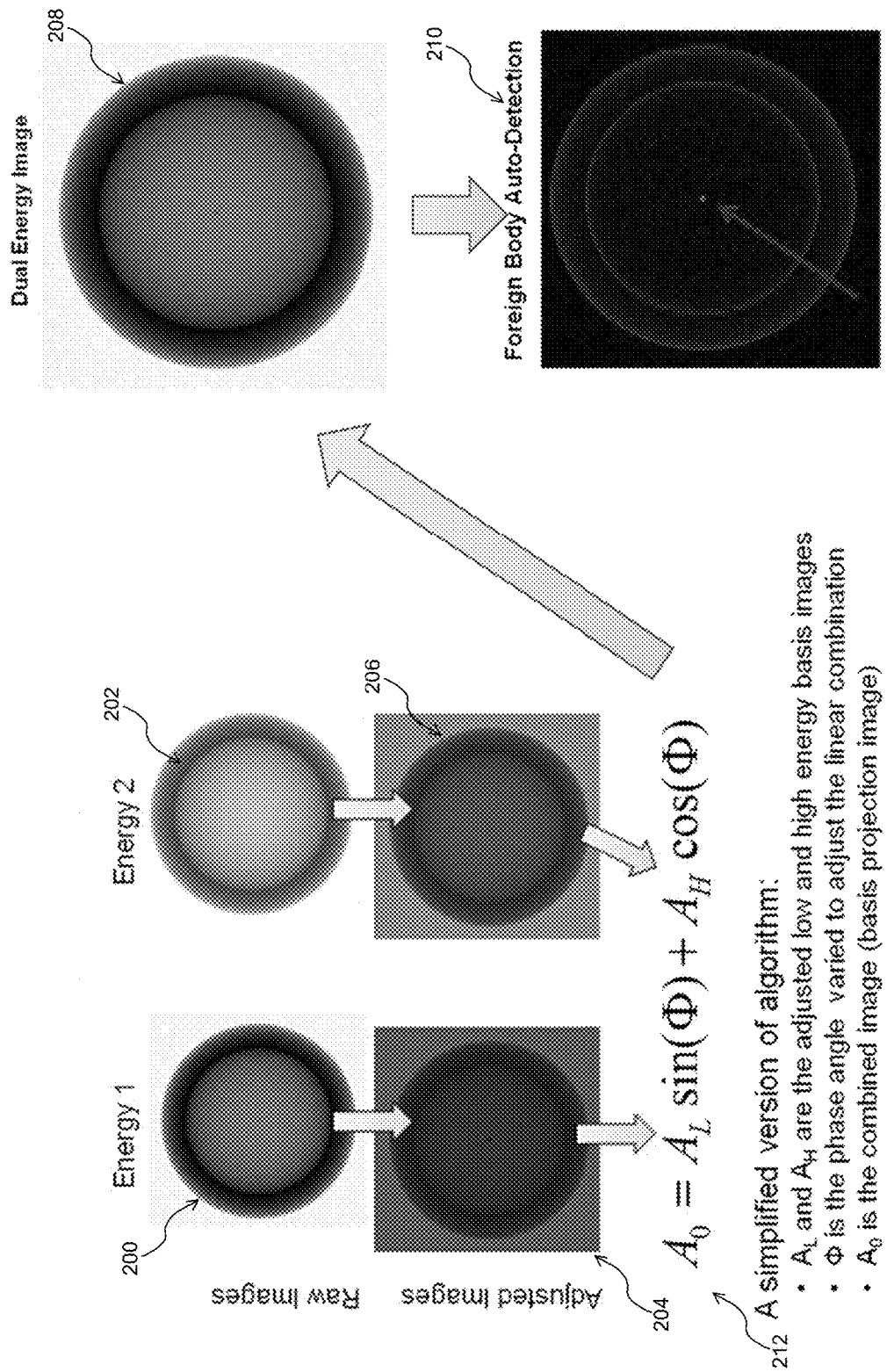
FIG. 2 is an illustration of a simplified dual-energy algorithm used in the system and method for detecting foreign objects in meat and poultry products in accordance with one embodiment of the subject application.
Figure 3:
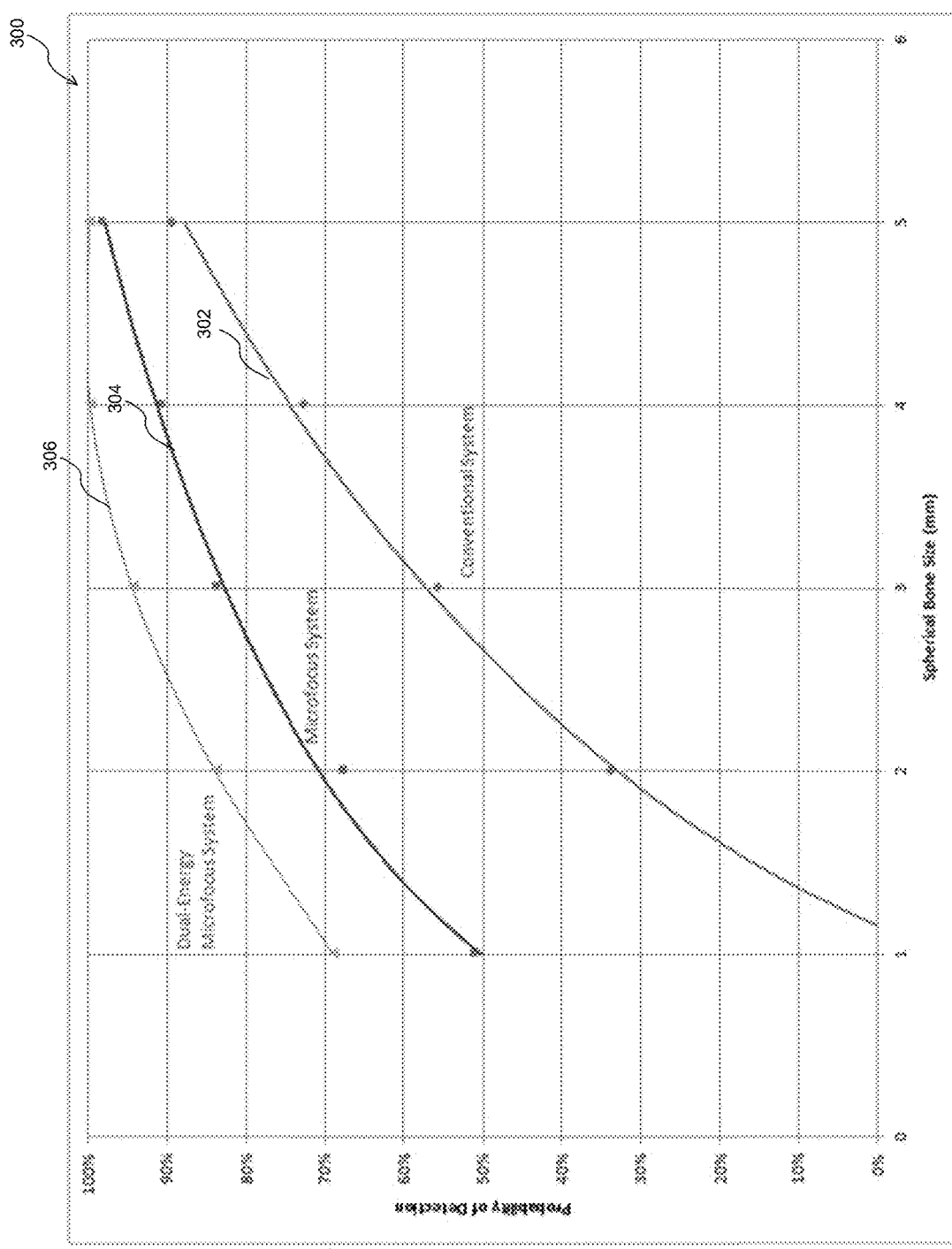
FIG. 3 is a graphical illustration of the probability of detection of contaminants using conventional, microfocus, and dual-energy microfocus techniques in accordance with one embodiment of the subject application.

The dual-energy microfocus algorithm 114 involves acquiring micro-focus images at two X-ray energies 106 (at a low and a high energy); then, processing these images to suppress the meat information revealing then the contaminate information. A simplified version of the algorithm (described in greater detail below) is illustrated in FIG. 2. As shown in FIG. 2, two different energy levels are used on the product 110. A first raw image 200 is generated from a first energy level and a second raw image 202 is generated from a second energy level. The raw images 200 and 202 are adjusted (as discussed below) to produce respective adjusted images 204 and 206. These adjusted images 204 and 206 are combined using the simplified algorithm 212 depicted in FIG. 2. As shown, the combined image 208 (basis projection image) ($A_0$) is calculated from the adjusted low energy basis image 204 ($A_L$) and the adjusted high energy basis image 206 ($A_H$) using the phase angle ($\phi$) varied to adjust the linear combination via the equation [$A_0 = A_L \sin(\phi) + A_H \cos(\phi)$]. Thereafter, foreign body detection 210 is performed, as set forth hereinafter.

It will be appreciated that the basic mathematical model assumes that the tube output radiation is known and that the scattered radiation is small. In this case, the transmitted radiation intensity through a region of inspected product meat (m) and/or contaminate (c), acquired at the lower (L) X-ray energy and following logarithmic transformation ($I_L$) is given by:

$$I_L = \mu_{mL} x_m + \mu_{cL} x_c,$$

where:

$\mu_{mL}$ is the linear attenuation coefficient, averaged over the tube radiation output spectrum, of the meat at the lower (L) X-ray energy;

$x_m$ is the meat thickness;

$\mu_{cL}$ is the linear attenuation coefficient of contaminate at the low X-ray energy; and $x_c$ is the contaminate thickness.

Similarly, the logarithmic transformation of the transmitted radiation intensity ($I_H$) for the same region of an image acquired at a higher X-ray energy is given by:

$$I_H = \mu_{mH} x_m + \mu_{cH} x_c,$$

where:

$\mu_{mH}$ is the linear attenuation coefficient of meat at the higher (H) X-ray energy; and $\mu_{cH}$ is the linear attenuation coefficient of contaminate at the higher (H) X-ray energy.

The attenuation factor for a given material (i) are an average over the tube output's low and high energy spectral outputs S(V). So, $$\mu_{iV} = \int_0^V \mu_i(E) \cdot S(E) dE / \int_0^V S(E) dE$$

where:

V is the tube voltage; high (H) and low (L) settings

E is the spectral energy from the tube's output at tube voltage (V)

$\mu_i(E)$ is the linear attenuation coefficient of a material as a function of the spectral energy (E).

The attenuation factor's energy function will also vary as a function of material's density (e.g., amount of water in the meat). Radiographic density analysis of the images during the measurement process will choose appropriate optimized values based on pre-existing charts coded into the algorithm.

Step 1: assume baseline value for $\mu_{iV}$

Step 2: obtain average radiographic density (d) at high and low energy $$d_{avg}^V = \int_i^{image} d_i^V di / T$$

and $$\mu_{iV}(\text{adjusted}) = f(d_{avg}^V)$$

where:

V is the high (H) or low (L) tube energy d is the measured radiographic density at $i^{th}$ pixel in the image.

T is the average meat thickness

Once the values for $\mu_{iL}$ and $\mu_{iH}$ are determined, the two images ($I_L$ and $I_H$) are multiplied by their respective weighting factors, $k_L$ and $k_H$. The two images are combined to form a composite dual-energy image ($I_{DE}$), given by:

$$I_{DE} = k_L I_L + k_H I_H.$$

Therefore:

$$I_{DE} = (k_L \mu_{mL} + k_H \mu_{mH}) x_t + (k_L \mu_{cL} + k_H \mu_{cH}) x_c, \quad (1)$$

The coefficients are chosen so to cancel the image information from the meat 108, leaving only the image information of the contaminants 110. So, the coefficient of $x_m$ is set equal to zero, i.e.:

$$k_L\mu_{mL}+k_H\mu_{mH}=0.$$

Thus, $$k_L\mu_{mL}=-k_H\mu_{mH},$$

and $$\mu_{mL}/\mu_{mH}=-k_H/k_L,$$

which indicates that tissue can be suppressed from the composite image when the ratio of weighting factors in equation (1) above is chosen to equal the negative of the ratio of the attenuation coefficients of tissue at the two X-ray energies. It will be appreciated that the meat information can never be completely eliminated, because the attenuation factors are an average over the tube outputs low and high energy spectral outputs, but depending on the specific energy levels chosen, tube type, amount of beam hardening, etc., an optimal ratio value can be obtained using the variational principle.

$$\delta \int_0^V \frac{\mu_{mL}}{\mu_{mH}} \partial V = 0$$

The above calculations in principle refer to an individual pixel reading on the detector 104, (pi) and are a function of detector's pixel size (p), the microfocus tube's spot size (s) and the radiographic magnification (RM) factor given by source-to-detector and source-to-product distance. The above calculations can be computed as either a function of these effects for each pixel in the detector 104 yielding a weighted average over the detector 104.

$\omega i=fi(p, s, RM)$ for each pixel i.

$$W_{avg}=\int_0^i f(p,s,RM)_i \cdot di/\int_0^i idi$$

$$I_{DE} \rightarrow W \cdot I_{DE}$$

Within the image of IDE, a contrast difference greater than or equal to a baseline optimal contrast Copt is necessary for a determination of a foreign object. Copt is chosen by the user. A foreign object 110 is detected if:

$$I_{DE} \rightarrow C > C_{opt}$$

The memory 122 may represent any type of non-transitory computer readable medium such as random access memory (RAM), read only memory (ROM), magnetic disk or tape, optical disk, flash memory, or holographic memory. In one embodiment, the memory 122 comprises a combination of random access memory and read only memory. In some embodiments, the processor 120 and memory 122 may be combined in a single chip. The network interface(s) 126, 128 allow the computer to communicate with other devices via a computer network, and may comprise a modulator/demodulator (MODEM). Memory 122 may store data the processed in the method as well as the instructions for performing the exemplary method.

The digital processor 120 can be variously embodied, such as by a single core processor, a dual core processor (or more generally by a multiple core processor), a digital processor and cooperating math coprocessor, a digital controller, or the like. The digital processor 120, in addition to controlling the operation of the image processing system 112, executes instructions 124 stored in memory 108 for performing the method outlined in FIG. 2.

The term "software," as used herein, is intended to encompass any collection or set of instructions executable by a computer or other digital system so as to configure the computer or other digital system to perform the task that is the intent of the software. The term "software" as used herein is intended to encompass such instructions stored in storage medium such as RAM, a hard disk, optical disk, or so forth, and is also intended to encompass so-called "firmware" that is software stored on a ROM or so forth. Such software may be organized in various ways, and may include software components organized as libraries, Internet-based programs stored on a remote server or so forth, source code, interpretive code, object code, directly executable code, and so forth. It is contemplated that the software may invoke system-level code or calls to other software residing on a server or other location to perform certain functions.

The image processing system 112 also includes one or more input/output (I/O) interface devices 124 and 126 for communicating with external devices. The I/O interface 124 may communicate with one or more of a display device 116, for displaying information, and a user input device 117, such as a keyboard or touch or writable screen, for inputting text, and/or a cursor control device, such as mouse, trackball, or the like, for communicating user input information and command selections to the processor 120. The various components of the image processing system 112 may all be connected by a data/control bus 128. The processor 120 of the image processing system 102 is in communication with an associated data storage 130 via a link 132. A suitable communications link 132 may include, for example, any suitable channel of data communications such as wireless communications, for example Bluetooth, WiMax, 802.11a, 802.11b, 802.11g, 802.11(x), a proprietary communications network, infrared, optical, the public switched telephone network, or any suitable wireless data transmission system, or wired communications. The data storage 130 is capable of implementation on components of the image processing system 112, e.g., stored in local memory 122, i.e., on hard drives, virtual drives, or the like, or on remote memory accessible to the image processing system 112.

The associated data storage 130 corresponds to any organized collections of data, e.g., radiographic data pictures in various file formats, including but not limited to, JPG, PNG, RAD, and BMP; algorithm software code in various file formats, including, but not limited to, FORTRAN and C (all versions); data sheets containing variables and data density constants in formats including, but not limited to, ASCII, Excel, and hard coded in above mention software code, and the like, used for one or more purposes. Implementation of the associated data storage 130 is capable of occurring on any mass storage device(s), for example, magnetic storage drives, a hard disk drive, optical storage devices, flash memory devices, or a suitable combination thereof. The associated data storage 130 may be implemented as a component of the image processing system 112, e.g., resident in memory 122, or the like.

As depicted in FIG. 1, the system 100 may include or communicate with one or more user access devices 116, depicted in FIG. 1 as a display device, e.g., a device capable of displaying a graphical user interface, which is capable of interacting with the image processing system 112 via a suitable link 150. Display device 116 is representative of any interfacing device, such as an integrated user interface physically coupled to the image processing system 112, or any personal computing device, such as a personal computer, a netbook computer, a laptop computer, a workstation computer, a personal data assistant, a web-enabled cellular telephone, a tablet computer, a proprietary network device, or other web-enabled electronic device. The data communications link 150 between the image processing system 112 and the display device 116 may be accomplished via any suitable channel of data communications such as wireless communications, for example Bluetooth, WiMax, 802.11a, 802.11b, 802.11g, 802.11(x), a proprietary communications network, infrared, optical, the public switched telephone network, or any suitable wireless data transmission system, or wired communications. When the display device 116 is implemented as a component of the image processing system 112, the communications link 150 may be similar to the bus 128, USB connectivity, HDMI, proprietary connectivity, or the like, enabling the bi-directional communication of data and instructions between the display device 116 and the processor 120 of the image processing system 112.

Although not shown, the display device 116 may include a processor, system memory, system storage, buses that couple various system components including the system memory to the processing unit, and the like. The display device 116 may be suitably configured to interact with the image processing system 112, to access the data storage 130, review output from the radiation detectors 104, direct operations of the microfocus X-ray tubes 102, identify the product 108, display the debris/contaminant 110, activate or shut off the alarm component 118, generate a graphical user interface, and otherwise interact with users, and the like. In embodiments wherein the display device 116 is separate from the image processing system 112, the display device 116 may include a web-browser, dedicated application, or other thin client interface, e.g., stored in memory, which is operable to interact with the image processing system 112. The thin client may be suitably configured to display the graphical user interface, display output of the radiation detectors 104, and the like. It will be appreciated that the processor and memory of such a standalone display device 116 can be configured as set forth above with respect to the processor 120 and memory 122 of the image processing system 112.

Experimental Results

A series of simulation models and experimental data were taken to validate the technique discussed above. As illustrated in FIGS. 3-9, discussed hereinafter, simulation data demonstrates that there is an increase in the probability of detection of foreign matter in meat in employing microfocus and dual-energy techniques as described herein. For purposes of illustration, the graph 300 of FIG. 3 was generated using simulation models to generate high and low energy radiographs of chicken meat with small bone fragments. The blue line 302 shows the effect of conventional system's ability to detect smaller sized fragments. The red line 304 shows the effect of a microfocus system's ability to detect smaller sized fragments. The green line 306 shows the effect of the dual-energy microfocus system 100 ability with respect to the detection of smaller sized fragments. It should be noted that there is an increase in the probability of detection when microfocus 304 and microfocus with dual-energy 306 techniques described above are employed.

Utilizing one implementation of the subject systems and methods, a series of experimental efforts were conducted to prove the technique valid. In these experiments, chicken meat was used, and three different types of foreign matter (bone, cartilage, and plastic) of sizes ranging from 1 to 5 mm in maximum size were used. As will be apparent from the results and figures set forth herein, the experimental efforts validated the simulation results and the microfocus dual-energy technique as described above was proven.

Figure 4:
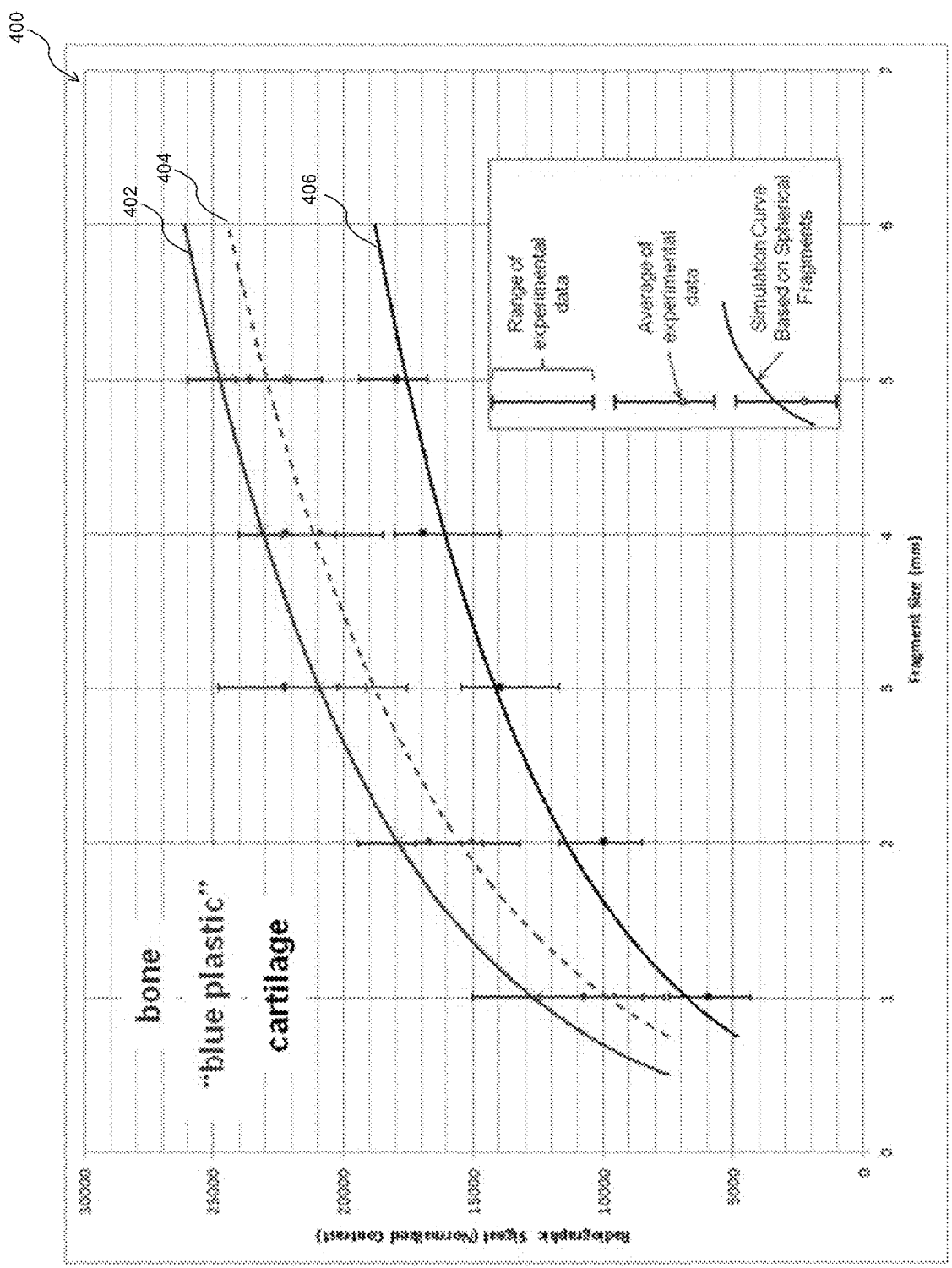
FIG. 4 is a graphical illustration of simulation and experimental results in accordance with one embodiment of the subject application.

FIG. 4 provides an illustrative graph 400 of simulation validation, depicting a comparison of the simulated results with the experimental results for bone 402, plastic 404 and cartilage 406. It will be appreciated that the simulated results and the experimental results are in substantial agreement.

Figure 5:
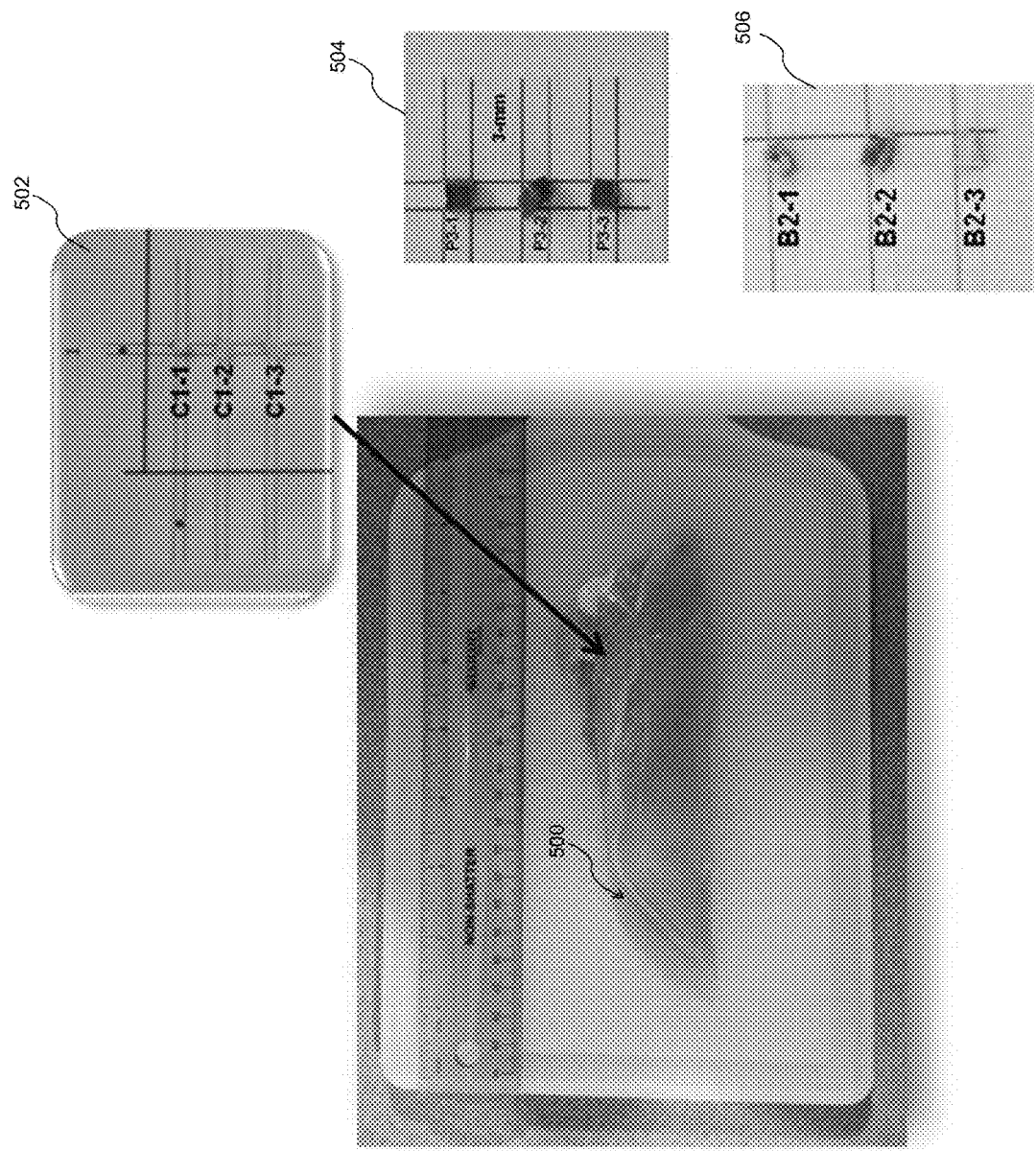
FIG. 5 is a photograph of a meat (poultry) product and various contaminants used in the experimental application of the system and method for detecting foreign objects using dual-energy microfocus in accordance with one embodiment of the subject application.

With reference to FIGS. 5-9, there are shown several examples of experimental results. Accordingly, FIG. 5 illustrates a sample chicken product 500 and three distinct types of foreign matter implanted into the product, e.g., cartilage fragments 502, plastic fragments 504, and bone fragments 506.

Figure 6:
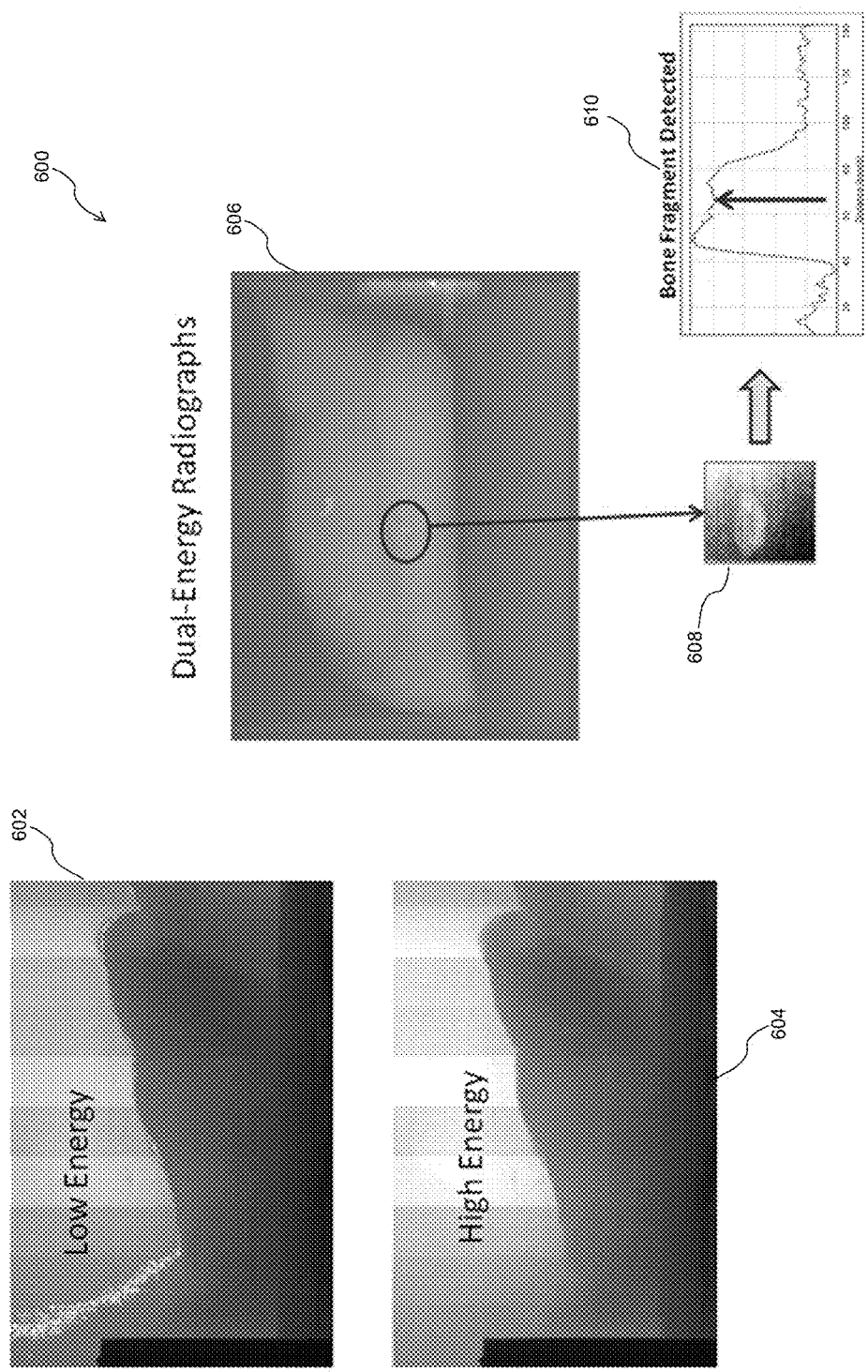
FIG. 6 is an illustration of individual radiographs and the corresponding dual-energy radiograph generated in accordance with one embodiment of the system and method for detecting foreign objects set forth in the subject application.

Referring now to FIG. 6, there is shown an illustration 600 of exemplary high 604 and low 602 energy radiographs and the resultant dual-energy radiograph 606 in accordance with one embodiment of the subject application. FIG. 6 further depicts the contrast measurement 610 used to identify the foreign particle, i.e. the bone fragment 608. It will be appreciated that in the example illustrated in FIG. 6, neither the high energy image 604 nor the low energy image 602 were individually capable of discerning the foreign contaminates 608.

Figure 7:
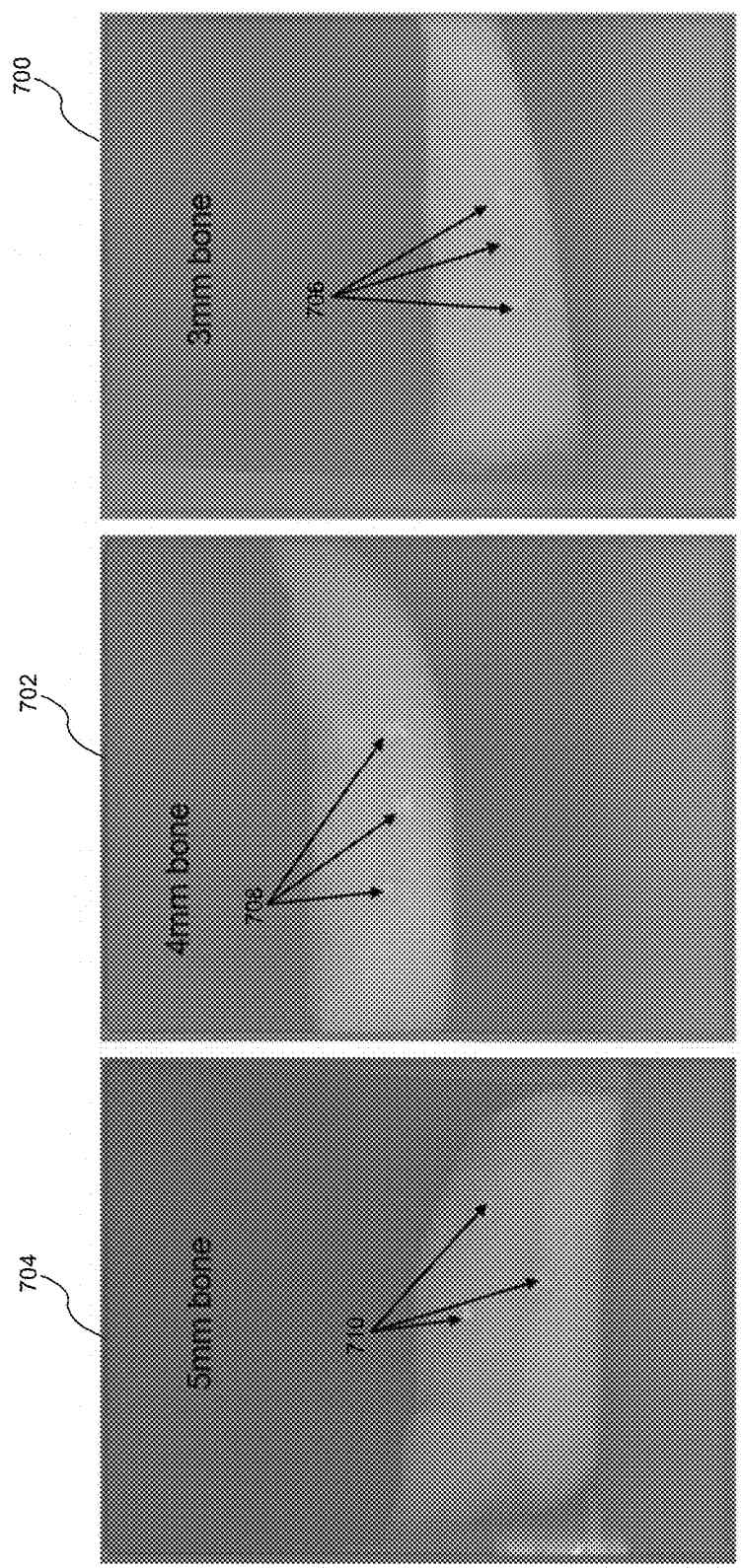
FIG. 7 is an illustration of radiographs of bone contaminants in poultry products generated in accordance with one embodiment of the system and method for detecting foreign objects set forth in the subject application.
Figure 8:
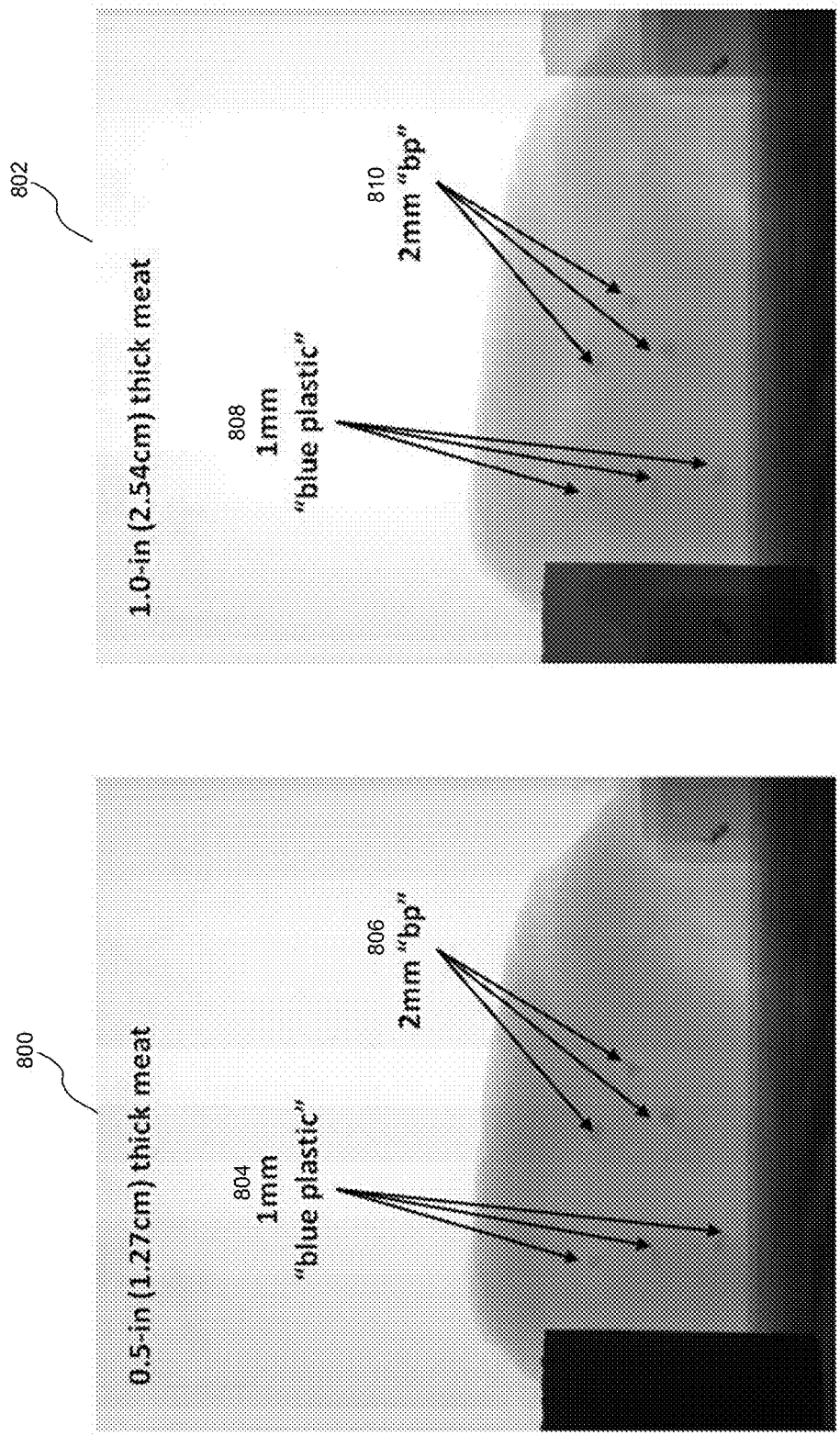
FIG. 8 is an illustration of radiographs of plastic contaminants in poultry products generated in accordance with one embodiment of the system and method for detecting foreign objects set forth in the subject application.
Figure 9:
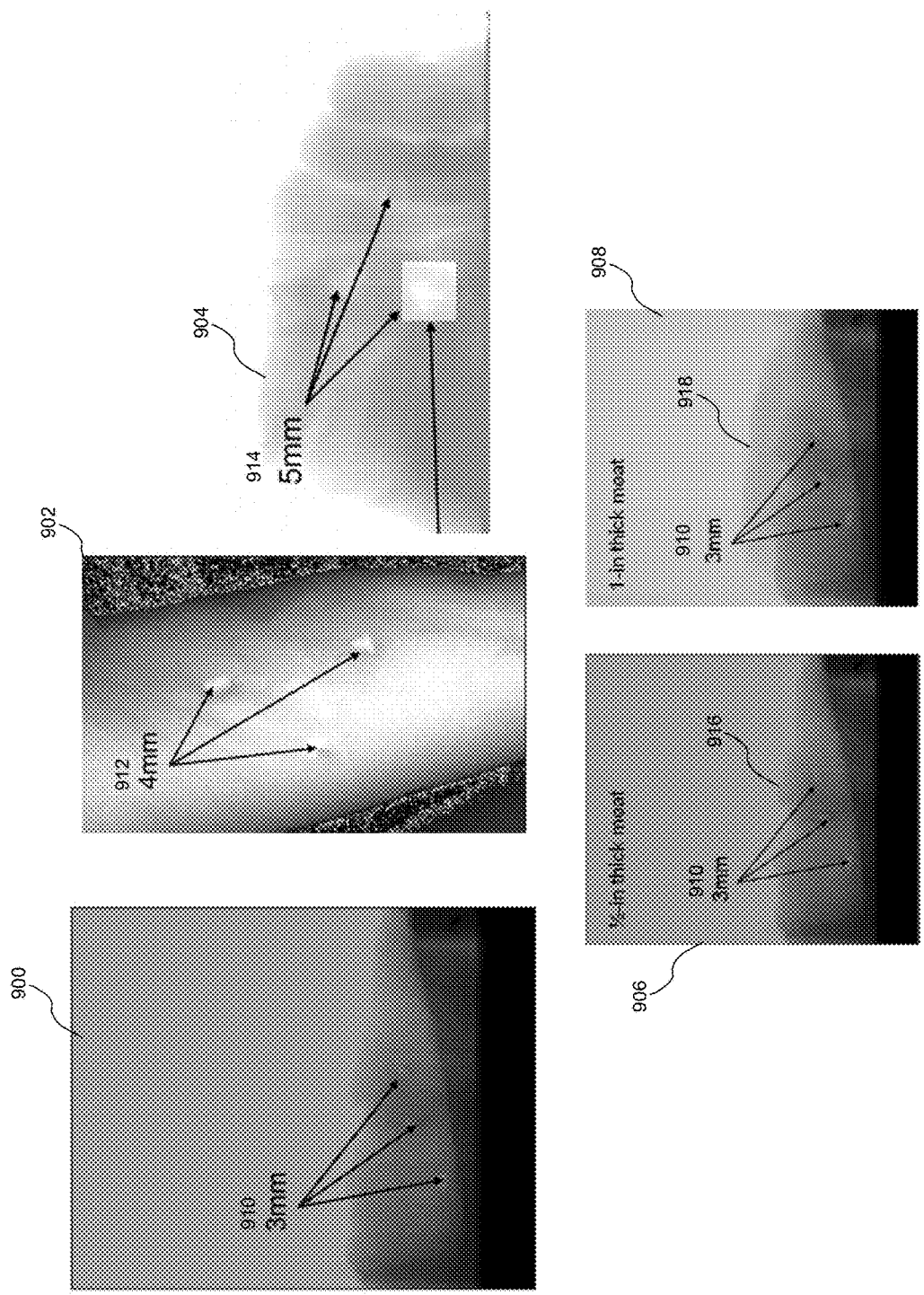
FIG. 9 is an illustration of radiographs of cartilage contaminants in poultry products generated in accordance with one embodiment of the system and method for detecting foreign objects set forth in the subject application.

Turning now to FIGS. 7 and 8, there are shown examples output images capable of detecting otherwise undetectable contaminants in accordance with the microfocus dual-energy systems and methods set forth above. FIG. 7 illustrates microfocus dual-energy radiographs 700, 702 and 704 generated by the system 100 according to one embodiment of the subject application. As shown, each radiographic image 700-704 illustrates different sized bone contaminants, respectively depicted at 706 (3 mm), 708 (4 mm), and 710 (5 mm). Similarly, FIG. 8 includes microfocus dual-energy radiographs 800 and 802 reflecting the detection of plastic contaminates 804-810 in accordance with one embodiment of the subject application. For example, the radiograph 800 depicts a one-half inch thick piece of poultry in which 1 mm plastic (804) and 2 mm plastic (806) contaminants are detected using the systems and methods described above. The radiograph 800 depicts a one inch thick piece of poultry in which 1 mm (808) and 2 mm (810) pieces of plastic have been detected. In addition to the foregoing, FIG. 9 includes microfocus dual-energy radiographs 900, 902, 904, 906, and 908 reflecting the detection of cartilage contaminants 910, 912, and 914 in accordance with one embodiment of the subject application. As shown in FIG. 9, the radiographs 900-904 depict cartilage contaminants 910 (3 mm), 912 (4 mm) and 914 (5 mm) detected via the systems and methods set forth in the subject disclosure. Radiograph 906 provides detection illustration of 3 mm cartilage fragments 910 in a ½ inch thick meat product 916. Similarly, the radiograph 908 provides detection illustration of 3 mm cartilage fragments 910 in a 1-inch thick meat product 918.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A system for foreign object detection in poultry processing, comprising:
    a first microfocus X-ray tube outputting a first X-ray energy;
    a second microfocus X-ray tube outputting a second X-ray energy, the second X-ray energy differing from the first X-ray energy;
    at least one radiation detector positioned opposite the first and second microfocus X-ray tubes to receive dual energy X-rays emitted by the first and second microfocus X-ray tubes through an associated poultry product;
    an image processing system including a processor in communication with memory, the memory storing instructions which are executed by the processor causing the processor to:
        receive an output from the at least one radiation detector of the dual energy X-rays through the associated poultry product,
        determine, in accordance with a dual energy algorithm, a presence of at least two different foreign objects in the associated poultry product, and
        generate an alarm responsive to determining the presence of the foreign object in the associated poultry product; and
    an object identifier module in communication with the processor, wherein for each foreign object present in the associated poultry product, the object identifier module identifies a type of foreign object detected in the associated poultry product as bone, cartilage, metal, or plastic in accordance with the dual energy algorithm.

2. The system for foreign object detection in poultry processing of claim 1, further comprising an X-ray controller in communication with the processor, wherein the X-ray controller selects the first X-ray energy and the second X-ray energy respectively emitted by the first and second microfocus X-ray tubes through the associated poultry product.

3. The system for foreign object detection in poultry processing of claim 2, further comprising an alarm component in communication with the image processing system, wherein the alarm component is selected from the group consisting of a speaker, a display, or a visual indicator.

4. The system for foreign object detection in poultry processing of claim 1, wherein the first and second microfocus X-ray tubes have a focal spot size in the range of 15 to 50 micrometers.

5. The system for foreign object detection in poultry processing of claim 2, wherein the at least one radiation detector is a small-pixel X-ray digital detector.

6. The system for foreign object detection in poultry processing of claim 2, further comprising a display in communication with the image processing system, wherein the instructions which are executed by the processor further cause the processor to:
    generate a graphical illustration of the associated poultry product on the display; and
    identify the foreign object in the associated poultry product on the graphical illustration on the display.

7. The system of claim 1, wherein the memory further stores instructions which are executed by the processor causing the processor to:
    generate a first energy image corresponding to the output from the at least one radiation detector of the first X-ray energy;
    generate a second energy image corresponding to the output from the at least one radiation detector of the second X-ray energy; and
    generate, in accordance with the dual energy algorithm, a combined image from the first and second energy images,
    wherein the presence of the two or more foreign objects in the associated poultry product is determined in accordance with the generated combined image.

8. A method for foreign object detection in poultry processing, comprising the steps of:
    emitting, through a first microfocus X-ray tube, X-rays at a first energy level through an associated poultry product;
    emitting, through a second microfocus X-ray tube, X-rays at a second energy level through the associated poultry product, the first energy X-rays and the second energy X-rays combined as dual energy X-rays, the first energy level differing from the second energy level;
    receiving, via at least one radiation detector, the dual energy X-rays transmitted through the associated poultry product;
    analyzing, with a processor in communication with memory storing a dual energy image processing algorithm, the dual energy X-rays received by the at least one radiation detector to identify at least two different foreign objects contained therein;
    identifying a type of each foreign object detected in the associated poultry product as bone, cartilage, metal, or plastic in accordance with the dual energy algorithm; and
    generating, in response to the analysis, an alarm indicative of a presence of a foreign object in the associated poultry product.

9. The method for foreign object detection in poultry processing of claim 8, wherein the alarm is selected from the group consisting of a speaker, a display, or a visual indicator.

10. The method for foreign object detection in poultry processing of claim 8, wherein the at least one radiation detector is a small-pixel X-ray digital detector.

11. The method for foreign object detection in poultry processing of claim 8, wherein the first and second microfocus X-ray tubes have a focal spot size in the range of 15 to 50 micrometers.

12. The method for foreign object detection in poultry processing of claim 8, further comprising:
generating, on an associated display in communication with the processor, a graphical illustration of the associated poultry product; and
identifying the foreign object in the associated poultry product on the graphical illustration on the display.

13. The method of claim 8, further comprising the steps of:
generating a first energy image corresponding to the output from the at least one radiation detector of the first X-ray energy;
generating a second energy image corresponding to the output from the at least one radiation detector of the second X-ray energy; and
generating, in accordance with the dual energy algorithm, a combined image from the first and second energy images,
wherein the presence of the two or more foreign objects in the associated poultry product is determined in accordance with the generated combined image.

14. A system for foreign object detection in meat processing, comprising:
at least one microfocus X-ray tube;
at least one radiation detector positioned opposite the at least one microfocus X-ray tube to receive dual energy X-rays emitted by the at least one microfocus X-ray tube through an associated meat product; and
an image processing system including a processor in communication with memory, the memory storing instructions which are executed by the processor causing the processor to:
receive an output from the at least one radiation detector of the dual energy X-rays through the associated meat product,
determine, in accordance with a dual energy algorithm, a presence of at least two different foreign objects in the associated meat product,
identify, for each foreign object present in the associated meat product, a type of foreign object selected from the group consisting of bone, cartilage, metal and plastic in accordance with the dual energy algorithm, and
generate an alarm responsive to determining the presence and identifying the type of each foreign object in the associated meat product.

15. The system for foreign object detection in meat processing of claim 14, further comprising an X-ray controller in communication with the processor, wherein the X-ray controller selects a first X-ray energy and a second X-ray energy to be emitted by the at least one microfocus X-ray tube through the associated meat product.

16. The system for foreign object detection in meat processing of claim 15, further comprising an alarm component in communication with the image processing system, wherein the alarm component is selected from the group consisting of a speaker, a display, or a visual indicator.

17. The system for foreign object detection in meat processing of claim 15, wherein the at least one radiation detector is a small-pixel X-ray digital detector.

18. The system for foreign object detection in meat processing of claim 14, wherein the at least one microfocus X-ray tube has a focal spot size in the range of 15 to 50 micrometers.

19. The system of claim 14, wherein the memory further stores instructions which are executed by the processor causing the processor to:
generate a first energy image corresponding to the output from the at least one radiation detector of the first X-ray energy;
generate a second energy image corresponding to the output from the at least one radiation detector of the second X-ray energy; and
generate, in accordance with the dual energy algorithm, a combined image from the first and second energy images,
wherein the presence of the two or more foreign objects in the associated poultry product is determined in accordance with the generated combined image.

20. A method for foreign object detection in meat processing, comprising the steps of:
emitting, through at least one microfocus X-ray tube, dual energy X-rays through an associated meat product;
receiving, via at least one radiation detector, the dual energy X-rays transmitted through the associated meat product;
generating, with a processor in communication with memory storing a dual energy image processing algorithm, a first energy image corresponding to the output from the at least one radiation detector of a first X-ray energy of the dual energy X-rays;
generating, with the processor, a second energy image corresponding to the output from the at least one radiation detector of a second X-ray energy of the dual energy X-rays;
generating in accordance with the dual energy image processing algorithm by the processor, a combined image from the first and second energy images;
analyzing, with the processor in communication with memory storing the dual energy image processing algorithm, the combined image to identify at least two distinct foreign objects contained therein;
identifying, for each foreign object identified in the associated meat product, a type of foreign object selected from the group consisting of bone, cartilage, metal and plastic in accordance with the dual energy algorithm; and
generating, in response to the analysis, an alarm indicative of a presence and a type of a foreign object in the associated meat product.

21. The method for foreign object detection in meat processing of claim 20, wherein emitting dual energy X-rays further comprises:
emitting an X-ray at a first energy level; and
emitting an X-ray at a second energy level, wherein the first energy level is different from the second energy level.

22. The method for foreign object detection in meat processing of claim 21, wherein the alarm is selected from the group consisting of a speaker, a display, or a visual indicator.

23. The method for foreign object detection in meat processing of claim 20, wherein the at least one radiation detector is a small-pixel X-ray digital detector.

24. The method for foreign object detection in meat processing of claim 20, further comprising:
- generating, on an associated display in communication with the processor, a graphical illustration of the associated meat product; and
- identifying the foreign object in the associated meat product on the graphical illustration on the display.

25. The method for foreign object detection in meat processing of claim 20, wherein the at least one microfocus X-ray tube has a focal spot size in the range of 15 to 50 micrometers.

* * * * *